(12) United States Patent
Kast et al.

(10) Patent No.: US 9,278,223 B2
(45) Date of Patent: *Mar. 8, 2016

(54) LEAD CONNECTOR WITH GLASS BRAZE

(71) Applicant: MEDTRONIC, INC., Minneapolis, MN (US)

(72) Inventors: John E. Kast, Hugo, MN (US); Darren A. Janzig, Center City, MN (US); Christopher J. Paidosh, St. Anthony, MN (US); Andrew J. Thom, Maple Grove, MN (US); Brad C. Tischendorf, Minneapolis, MN (US); Gerald G. Lindner, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,584

(22) Filed: May 5, 2014

(65) Prior Publication Data

US 2014/0243942 A1  Aug. 28, 2014

Related U.S. Application Data

(63) Continuation of application No. 13/012,979, filed on Jan. 25, 2011, now Pat. No. 8,751,002.

(60) Provisional application No. 61/299,167, filed on Jan. 28, 2010.

(51) Int. Cl.
*A61N 1/375* (2006.01)
*H01R 13/187* (2006.01)
*H01R 24/58* (2011.01)
*H01R 107/00* (2006.01)

(52) U.S. Cl.
CPC ............ *A61N 1/3752* (2013.01); *H01R 13/187* (2013.01); *H01R 24/58* (2013.01); *H01R 2107/00* (2013.01); *H01R 2201/12* (2013.01); *Y10T 29/49211* (2015.01)

(58) Field of Classification Search
USPC .......................................................... 607/37
See application file for complete search history.

(56) References Cited

U.S. PATENT DOCUMENTS

2001/0055716 A1* 12/2001 Frysz et al. .................... 429/184
2008/0208277 A1   8/2008 Janzig
2008/0208279 A1*  8/2008 Janzig et al. .................... 607/37

* cited by examiner

*Primary Examiner* — Carl H Layno
*Assistant Examiner* — Jon Eric C Morales
(74) *Attorney, Agent, or Firm* — Mueting, Raasch & Gebhardt, P.A.

(57) ABSTRACT

A medical device lead connector includes two or more electrically conducting contact rings spaced apart by electrically insulating ceramic ring. An electrically insulating glass material fixes the two or more electrically conducting contact rings to the insulating ceramic ring in axial alignment.

17 Claims, 7 Drawing Sheets

LEAD CONNECTOR WITH GLASS BRAZE

CROSS-REFERENCE

The present application is a continuation application of U.S. application Ser. No. 13/012,979, now U.S. Pat. No. 8,751,002 titled LEAD CONNECTOR WITH GLASS BRAZE, filed on Jan. 25,2011 which claims the benefit U.S. Provisional Application No. 61/299,167, filed on Jan. 28, 2010, of which all are hereby incorporated by reference in their entirety.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The lead connector block is often affixed to the hermetically sealed housing with brackets, and/or a medical grade adhesive.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Many such feedthroughs are known in the art that provide the conductive path and seal the electrical container from its ambient environment. Such feedthroughs typically include a ferrule, and an insulative material such as a hermetic glass or ceramic seal that positions and insulates the pin within the ferrule. Sometimes it is desired that the electrical device include a capacitor within the ferrule and around the terminal, thus shunting any electromagnetic interference (EMI) at high frequencies at the entrance to the electrical device to which the feedthrough device is attached. Typically, the capacitor electrically contacts the pin lead and the ferrule. While this arrangement has proven to be highly reliable, it involves a variety of expensive manufacturing processes and parts that necessarily increase the cost of the resulting product and increases the number of interconnects.

BRIEF SUMMARY

The present disclosure relates to lead connectors with glass braze. In particular the present disclosure relates to hermetic lead connectors that have contact portions separated by a ceramic insulating ring and joined together with electrically insulating glass material. The electrically insulating glass material can form a hermetic bond with the electrically conducting contact portions of the hermetic lead connectors.

In one illustrative embodiment, a medical device lead connector includes two or more electrically conducting contact rings spaced apart by an electrically insulating ceramic ring. An electrically insulating glass material fixes the two or more electrically conducting contact rings to the insulating ceramic ring in axial alignment.

In another illustrative embodiment, an implantable active medical device includes a hermetically sealed housing defining a sealed housing interior, a power source, and electronics in electrical communication and disposed within the sealed housing interior, and a lead connector projecting or extending into the sealed housing interior. The lead connector includes having a closed end, an open end, an outer surface, and an inner surface defining a lead aperture. The lead connector includes one or more electrically conducting contact rings spaced apart by electrically insulating rings and joined or coupled together with electrically insulating glass braze. The one or more electrically conducting contact rings are in electrical communication with the electronics, and the glass braze provides a hermetic seal between the lead connector outer surface and the lead connector inner surface.

In a further illustrative embodiment, a method of forming a medical device lead connector includes joining an electrically conducting contact ring to a ceramic insulating ring with a first glass braze material having a first glass transition temperature to form a first joined element and joining an electrically conducting spacer ring to the ceramic insulating ring of the first joined element with a second glass braze material having a second glass transition temperature to form a second joined element. In this exemplary embodiment the second glass transition temperature is less than the first glass transition temperature.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
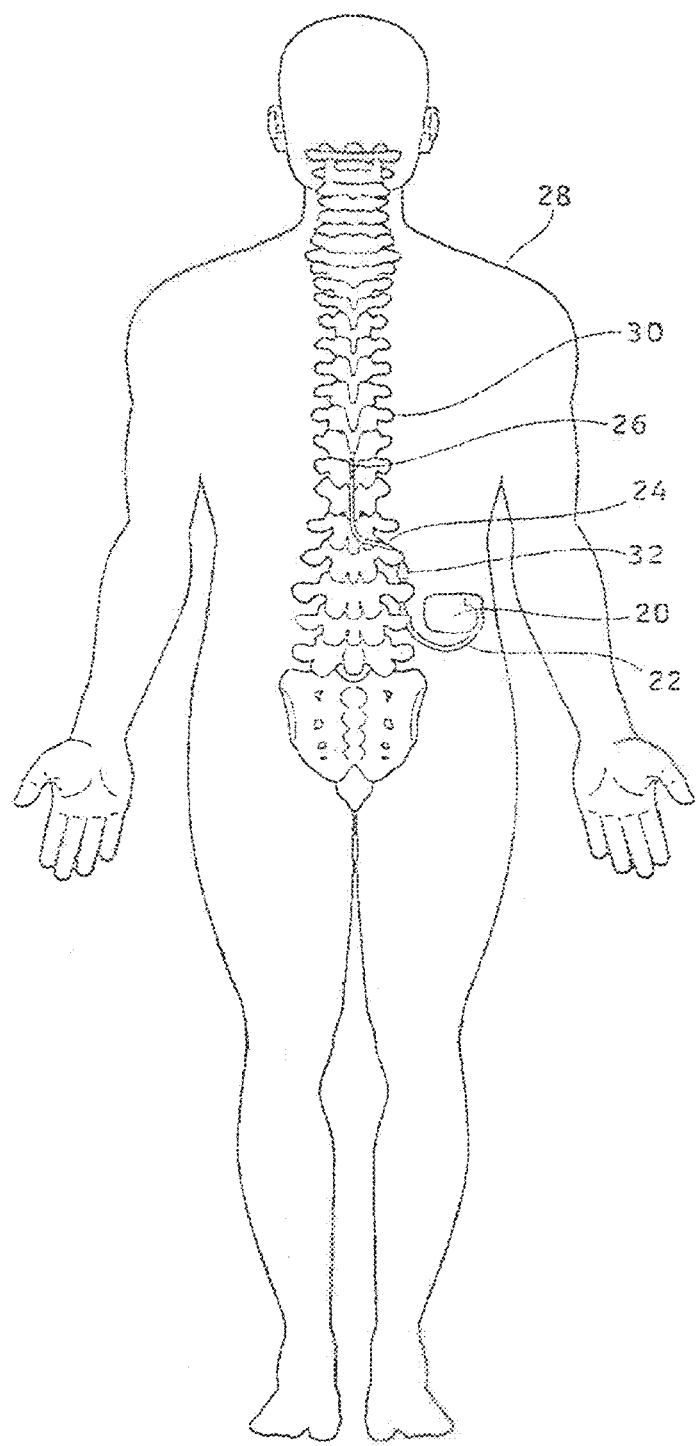
FIG. 1 is a schematic diagram of a an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to hermetic lead connectors with glass braze. In particular the present disclosure relates to hermetic lead connectors that have contact portions separated by electrically insulating portions and joined together with electrically insulating glass material. The electrically insulating glass material forms a hermetic bond with the electrically conducting contact portions and the electrically insulating portions of the hermetic lead connectors. The electrically insulating glass material eliminates gold or metal brazing material from the hermetic lead connector and thus the manufacturing temperatures of the hermetic lead connector is reduced, in many embodiments, to less than 875 degrees centigrade or a temperature at or about the glass transition temperature of the electrically insulating glass material. In addition, the electrically insulating glass material allows the electrical contact portions of the hermetic lead connector to be closer than has been conventionally available. For example, the pitch between electrical contact portions can be reduced to 0.085 inch or less. Utilizing electrically insulating glass material can provide a number of advantages such as reducing the manufacturing temperature and reducing the size of the hermetic lead connectors, for example, but not all advantages are necessarily present in all contemplated embodiments. While the present disclosure is not so limited, an appreciation of various aspects of the disclosure will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any suitable region of the body such as in the abdomen of a patient 28, and the lead 24 is shown placed somewhere along the spinal cord 30. In many embodiments, the active medical device 20 has one or two leads each having four to eight electrodes. Such a system may also include a physician programmer and a patient programmer (not shown). The active medical device 20 can be considered to be an implantable signal generator of the type available from Medtronic, Inc., and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces-Quad® lead available from Medtronic, Inc.), and some are designed to be surgically implanted (e.g. Model 3998 Specify® lead, also available form Medtronic, Inc.). In some embodiments, the lead 24 may contain a paddle at its distal end for housing electrodes 26. In many embodiments, electrodes 26 may include one or more ring contacts at the distal end of lead 24.

Figure 2:
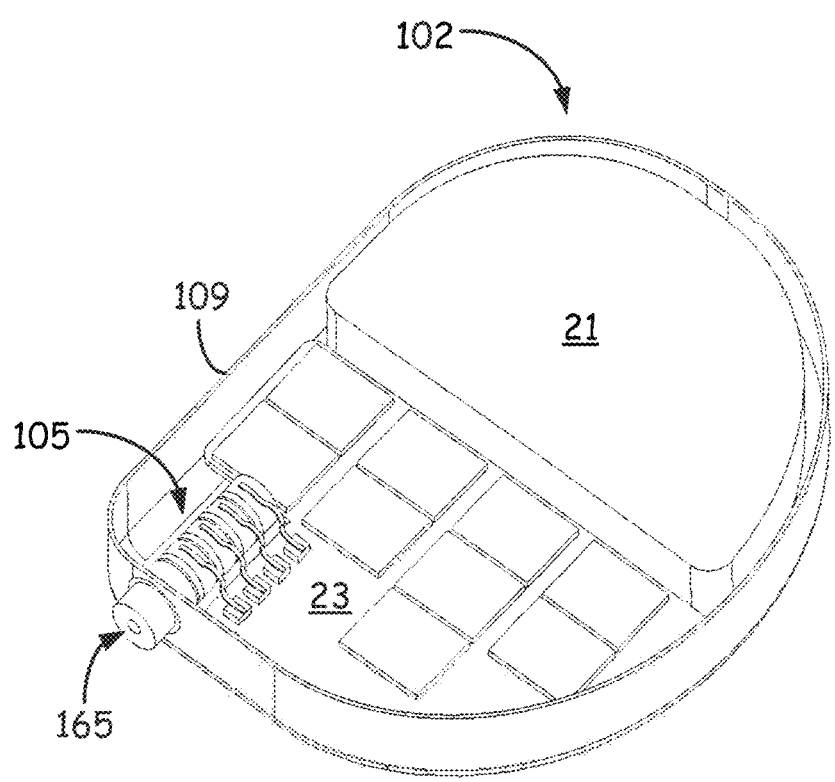
FIG. 2 is a schematic perspective view of an implantable active medical device with an internal hermetic lead connector.
Figure 3:
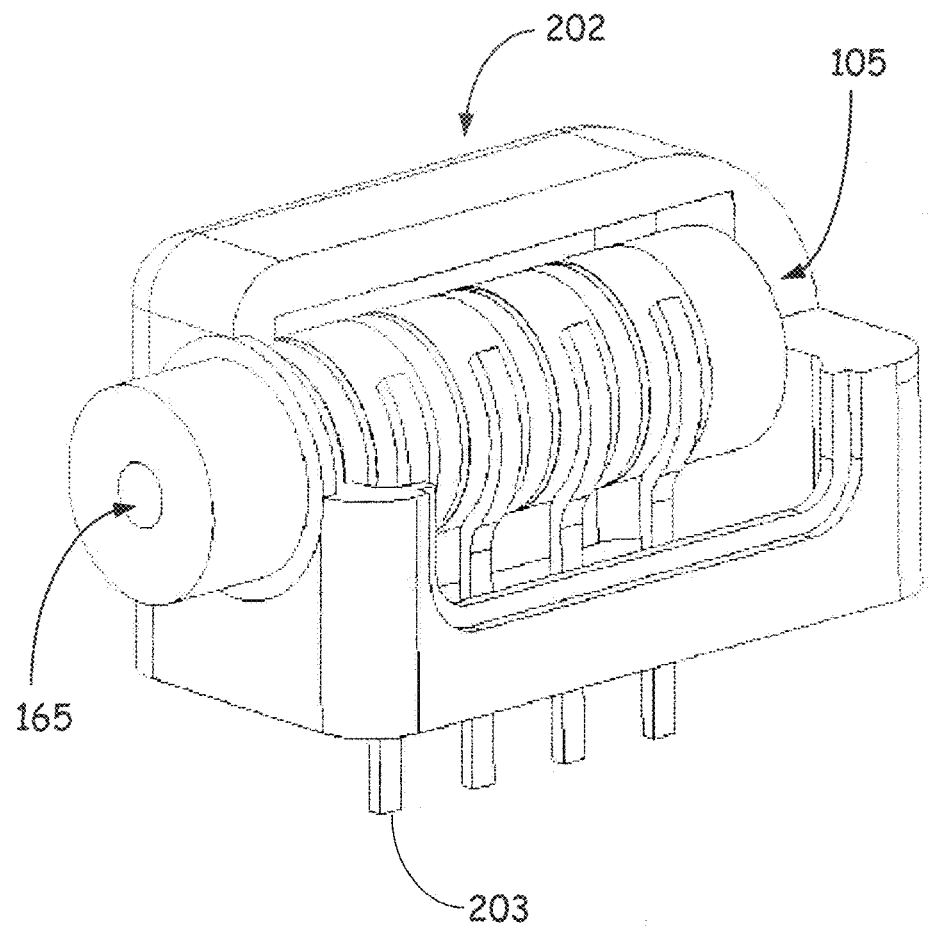
FIG. 3 is a schematic perspective view of another implantable active medical device with an external lead connector.

FIG. 2 is a schematic perspective view of an implantable active medical device 102. FIG. 3 is a schematic cut-away perspective view of an implantable active medical device header 202 with an external hermetic lead connector. Thus the disclosed lead connector 105 can be utilized in a conventional device that utilizes a feedthrough 203 to provide the hermetic barrier (see FIG. 3) or the disclosed lead connector 105 can be utilized to provide the hermetic barrier extending into a device (see FIG. 2). FIG. 3 does not show the hermetic enclosure for the electronics and power source, but it is understood that the hermetic enclosure would be adjacent to the feedthrough 203. FIG. 3 does not rely on the disclosed lead connector 105 to provide the device hermetic barrier, however the disclosed lead connector 105 provides a rigid lead connector with electrical contacts at a fixed pitch.

Figure 4:
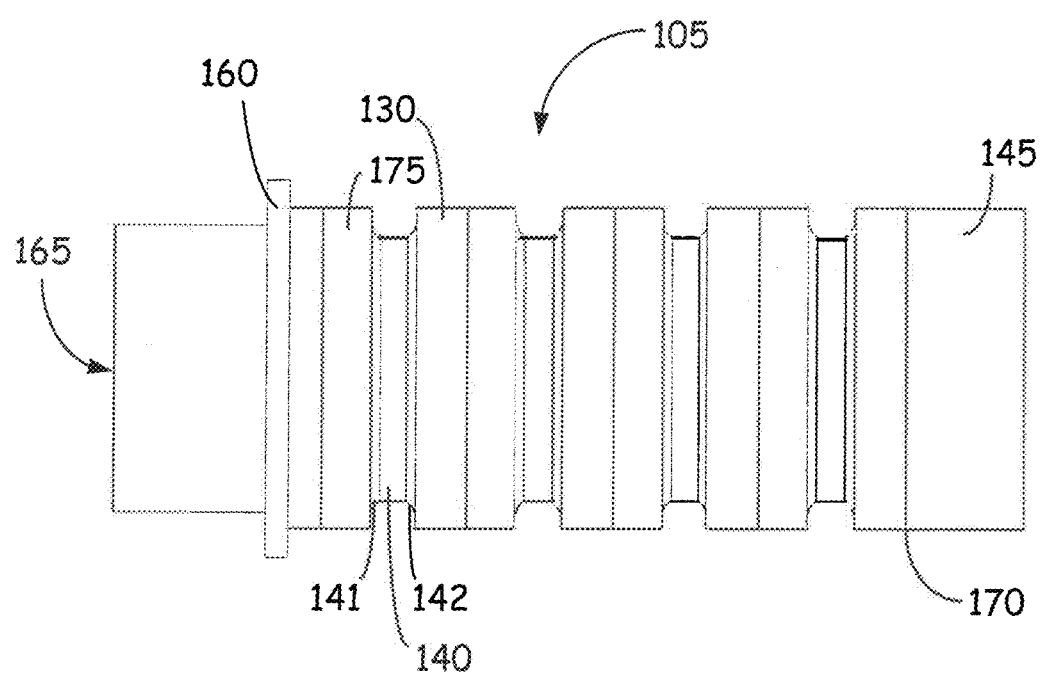
FIG. 4 is a schematic diagram side elevation view of an illustrative lead connector.
Figure 5:
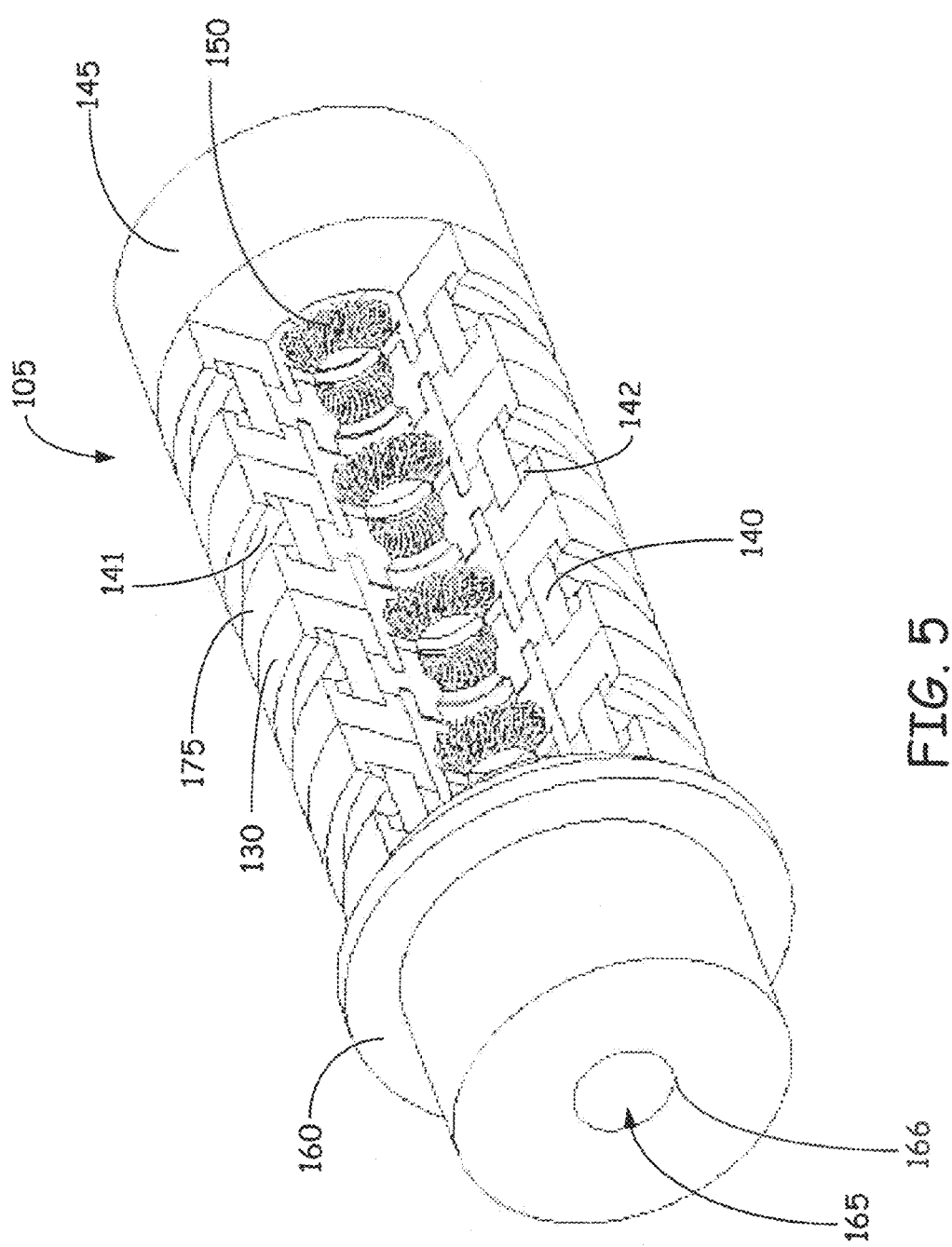
FIG. 5 is an perspective cut-away view of the illustrative lead connector shown in FIG. 4.
Figure 6:
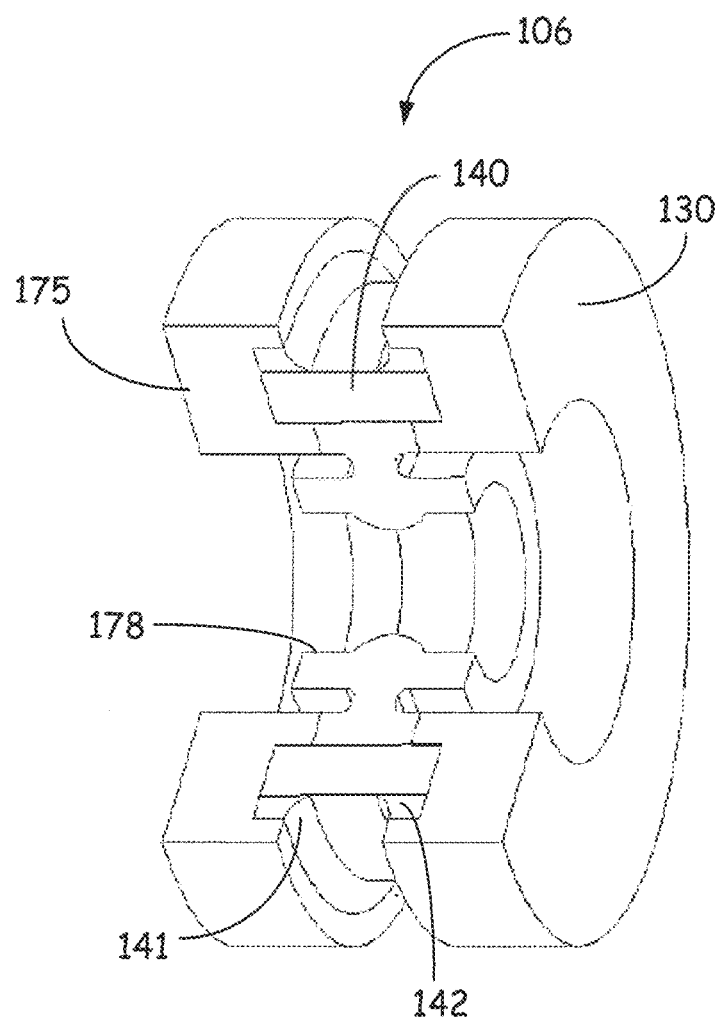
FIG. 6 is an perspective cut-away view of one of the illustrative lead connector sub-assemblies shown in FIG. 5.

FIG. 4 is a schematic diagram side elevation view of an illustrative lead connector 105. FIG. 5 is a perspective cut-away view of the illustrative lead connector 105 shown in FIG. 4. FIG. 6 is a perspective cut-away view of one of the illustrative lead connector sub-assemblies shown in FIG. 5.

The active medical device 102 includes a hermetically sealed housing 109 defining a sealed housing interior. The active medical device 102 is illustrated without a cover portion that would complete the hermetic sealed housing 109. A power source 21 and electronics 23 are in electrical communication and are disposed within the sealed housing 109 interior. A lead connector 105 projects into and through the sealed housing 109 interior and has an inner surface or lead receptacle defining an open lumen lead aperture 165. In many embodiments an outer surface of the lead connector 105 at least partially defines the sealed housing interior surface.

The lead connector 105 includes one or more electrically conducting contact rings 130 spaced apart by electrically insulating ceramic material 140. A first glass braze material 141 joins the ceramic ring 140 to the electrical contact ring 175. A second glass braze material 142 joins the ceramic ring 140 to the electrical contact ring 130. These elements form a subassembly 106 that can be welded together at the electrical contacts 130, 175 to form the lead connector 105.

The one or more electrically conducting contact rings 130 can be formed as a single element (not shown) or can include a second electrically conducting contact ring 175 that can be welded to the electrically conducting contact ring 130 to form the one or more electrically conducting contact rings 130, 175 as illustrated in the sub-assembly manufacture process described herein.

The one or more electrically conducting contact rings 130, 175 are in electrical communication with the electronics 23 and the lead connector 105 provides a hermetic seal between the sealed housing 109 interior and the lead aperture 165. The electronics 23 generally control the active medical device 102. The power source 21 can be any useful battery or power source such as an inductive coil. In some embodiments, the electronics 23 includes memory. The memory can be any magnetic, electronic, or optical media, such as random access memory (RAM), read-only memory (ROM), electronically-erasable programmable ROM, flash memory, or the like.

The one or more electrically conducting contact rings 130, 175 can be formed of any suitable electrically conductive material. In many embodiments, the one or more electrically conducting contact rings 130, 175 are formed of a metallic material such as, for example, titanium, stainless steel, MP35N, niobium, tantalum, platinum, and alloys or combinations thereof. In some embodiments, the one or more electrically conducting contact rings 130, 175 are formed of a metallic material such as, for example, titanium.

The ceramic ring 140 can be formed of any useful electrically insulating ceramic material. In many embodiments the ceramic ring 140 is rigid and is bonded to the electrically conducting contact rings 130, 175 via the electrically insulating glass braze material 141, 142. The electrically insulating glass braze material 141, 142 can be formed of any suitable electrically insulating glass material. Glass for formation of electrical insulating braze 141, 142 includes boro-alumino, boro-alumino silicate and/or boro silicate type glasses. The element(s) and/or compounds used to form electrical insulating braze material 141, 142 are selected in a manner preferably to reduce tensile stresses with conducting contact rings 130 and the ceramic ring 140. For example, electrical insulating braze material 141, 142, employing glass, can have a coefficient of thermal expansion (CTE) value about equivalent to or within 15% of the CTE associated with conducting contact rings 130 and the ceramic ring 140.

The electrical insulating braze material 141, 142 may be formed from a glass preform. For example, in making a lead connector 105, the glass preform may be melted so that the molten glass engages conducting contact rings 130, 175 and ceramic ring 140 and subsequently cooled to form subassembly 106. The glass preform can have a composition including about 30-40% $B_2O_3$, about 0-20% CaO, about 0-20% MgO, about 0-20% SrO, about 0-5% $La_2O_3$, about 5-10% $SiO_2$, and about 10-20% $Al_2O_3$, where all percentages represent mole percents. In some embodiments, the composition includes up to about 10% of $MnO_2$, and in some cases the $MnO_2$ may be about 15%. In some embodiments, all or some of the amounts of CaO and/or MgO are replaced with a corresponding amount of SrO, where the amount of SrO does not exceed about 40%. For example, about 10% of CaO and about 5% MgO may be replaced with about 15% SrO. However, the amounts of CaO and MgO are not entirely replaced by SrO, and none of CaO, MgO, and SrO is above 30%. In some embodiments, the composition includes about 30% $B_2O_3$, about 20% CaO, about 20% MgO, about 5% $La_2O_3$, about 10% $SiO_2$, and about 15% $Al_2O_3$.

Various components of the glass composition provide features in making a hermetic lead connector 105 and provide the resulting hermetic lead connector 105 with advantageous properties. In particular, $La_2O_3$ provides for better glass flow in melting and forming the electrical insulating braze material 141, 142, as lower temperatures may be employed compared to glass without $La_2O_3$ or with less $La_2O_3$. Lanthanum oxide also increases the coefficient of thermal expansion (CTE) value of the glass. For example, glass with little or no lanthanum oxide may have a CTE of about 6.5, where glass with lanthanum oxide as described herein may have a CTE of about 8.0. The increased CTE values are closer to the CTE values for metals, such as niobium (Nb), titanium (Ti), platinum (Pt), iridium (Ir) and/or alloys thereof. Similar CTE values reduce the resulting compressive force applied to the glass insulating member when disposed within a subassembly 106. Excessive force may contribute to tensile cracks in the glass insulating braze material 141, 142. The propensity for such tensile cracks may be reduced by employing the present compositions.

Strontium oxide within the composition also lowers the processing temperature. For example, as described above, some of the amounts of CaO and/or MgO may be replaced with a corresponding amount of SrO. In this way, the processing temperature of the glass composition may be adjusted, for example, in order to offset temperatures necessary to process amounts of silicon dioxide.

The present composition also limits the amount of $SiO_2$ to about 10%, as this amount provides long-term durability but does not substantially increase the processing temperature. For example, $SiO_2$ in the range of 20% or more increases the temperature required for processing the glass to the point where titanium, which can be used, for example, in conducting contact rings 130, 175, undergoes a phase transition. This may contribute to titanium parts, or other metal parts approaching the respective metal or alloy melting temperature, to subsequently warp or become distorted. Thus, the present glass composition keeps the amount of silicon dioxide amount low to allow lower processing temperatures where integrity of titanium portion(s) of the hermetic lead connector 105 are maintained.

In some embodiments, the electrically insulating glass braze material 141, 142 is formed of glass material including: 30 mol % $B_2O_3$; 30 to 40 mol % CaO, MgO, SrO, or combinations thereof; 5 mol % $La_2O_3$; 10 mol % $SiO_2$; and 15 mol % $Al_2O_3$. In many embodiments, the glass insulating material has a glass transition temperature of less than 875 degrees centigrade or has a glass transition temperature in a range from 550 to 700 degrees centigrade.

Other useful glass compositions are described in U.S. Pat. Nos. 5,821,011, 6,090,503, 6,855,456, 5,104,755, and 5,175,067, the disclosure of each of which is incorporated by reference herein. One useful class of glass compositions include BiZnB (bismuth, zinc, boron) glass compositions that can have a glass transition temperature of less then 700 degrees centigrade, or less then 500 degrees centigrade, or less then 350 degrees centigrade. One commercially available BiZnB glass compositions is available under the trade designation DM2995PF from DieMat, Inc. (Byfield, Mass.).

In some embodiments, a filtering capacitor is disposed between the electrically conducting contact rings 130, 175 and the electronics 23. The filtering capacitor can effectively filter out undesirable electromagnetic interference (EMI) from the active medical device 102.

The implantable active medical device described herein can eliminate the need for a conventional separate feedthrough block that electrically connects a conventional lead connector block with the hermetically sealed electronics of the implantable active medical device. By placing the lead connector within the hermetically sealed active medical device housing, a direct electrical connection between the lead connector and the electronics can be made (as illustrated in FIG. 2). In addition, the elimination of a feedthrough can reduce the size and volume of the implantable active medical device and can also reduce the number of parts and connections needed to assemble the implantable active medical device.

The illustrated lead connector 105 is an elongate member extending between a lead aperture 165, first open end 166, and end cap 145, and having an inner surface defining an open lumen lead aperture 165. The open lumen lead aperture 165 or lead receptacle 165 is configured to accept one a leads or lead extension, as described above, and electrically couple one or more lead contacts with one or more connector contacts 130, 175 that form the elongate body of the lead connector 105, that in many embodiments is generally cylindrical.

In many embodiments, the lead aperture 165 is a cylindrical open lumen of generally circular cross-sectional area formed by an inner surface of the electrically conducting rings 130, 175 and electrically insulating ceramic rings 140 bonded together with glass braze 141, 142, in axial alignment. The lead connector 105 defines a lead connector outer surface 170 and at least a portion of the lead connector outer surface 170 is disposed within the sealed housing 109 interior. In many embodiments, at least a majority of the lead connector outer surface 170 is disposed within the sealed housing 109 interior. In many embodiments, substantially the entire lead connector outer surface 170 is disposed within the sealed housing 109 interior and at least partially defines the sealed housing 109 interior. In some embodiments, the entire lead connector outer surface 170 is disposed within the sealed housing 109 interior.

In the illustrated embodiment, the lead connector 105 is formed of one or more electrically conducting contact rings 130, 175 spaced apart by electrically insulating ceramic rings 140 bonded together with glass braze 141, 142. The one or more electrically conducting contact rings 130 are in electrical communication with the electronics (described above), and the lead connector 105 body provides a hermetic seal between the sealed housing interior/lead connector outer surface 170 and the lead aperture 165. The one or more electrically conducting contact rings 130, 175 and electrically insulating ceramic rings 140 are assembled in axial alignment to form the lead connector 105.

The one or more electrically conducting contact rings 130, 175 can include one or more additional contact elements in electrical contact with and optionally disposed within each of the one or more electrically conducting contact rings 130, 175. These one or more additional contact elements are configured to provide electrical communication between one or more electrically conducting contact rings 130, 175 and a lead contact received within the lead aperture 165. In many embodiments, these contact elements are electrically conductive and resilient to provide an interference fit between the electrically conducting contact ring 130, 175 and lead contact received within the lead aperture 165.

Examples of contact elements include, but are not limited to, spring elements. In many embodiments, the contact element includes an annular helical coil 150 (i.e., continuous coil spring 150) disposed adjacent an inner surface of the electrically conducting contact ring 130. The helical annular coil 150 can be formed of any suitable electrically conductive material such as, for example, a metal like gold, silver, titanium or the like. When a lead in inserted into the lead aperture 165, the lead and lead contact(s) can deflect the annular helical coil 150 and form an electrical contact between the lead contact and the electrically conducting contact ring 130. The continuous coil spring 150 frictionally provides an electrical and mechanical engagement with a lead contact and the adjacent electrically conducting contact ring 130.

A mounting flange 160 can be fixed to the lead connector 105 adjacent the open end 166. The mounting flange 160 can be brazed or welded, for example, to the hermetically sealed housing 109. In some embodiments, the mounting flange 160 is brazed or welded to an exterior surface of the hermetically sealed housing 109. In other embodiments, the mounting flanges 160 are brazed or welded to an interior surface of the hermetically sealed housing 109. A retention member (not shown) such as for example, a set screw, can be disposed on the lead connector 105 adjacent to the open end 166 and can assist in mechanical retention of the lead disposed within the lead aperture 165.

The lead connector 105 can be formed by any suitable method. In many embodiments, the lead connector 105 is formed by assembling two or more lead connector subassemblies 106. FIG. 6 is a cut-away perspective cut-away view of the illustrative subassembly 106 shown in FIG. 4. Each lead connector subassembly 106 can be arranged in axial alignment and bonded utilizing a metal-to-metal bonding technique such as, for example, laser welding, to form the lead connector 105.

In the exemplary embodiment shown, each lead connector subassembly 106 includes an electrically insulating ceramic ring 140 fixed between the electrically conducting contact ring 130 and an attachment ring or electrically conducting spacer ring 175 with glass braze 141, 142. Thus, the electrically conducting spacer ring 175 is affixed to a first side of the electrically insulating ceramic ring 140 with a first glass braze 141 and the electrically conducting contact ring 130 is affixed to a second opposing side of the electrically insulating ceramic ring 140 with a second glass braze 142. The glass braze 141, 142 assists in creating the hermetic seal between the between the sealed housing interior/lead connector outer surface 170 and the lead aperture 165. In some embodiments, the subassembly 106 includes a wiper seal 178 that can assist in electrical isolation of adjacent electrical contacts and also to mitigate fluid transmission within the lead aperture.

In many embodiments the first glass braze 141 has a different glass transition temperature than the second glass braze 142. In some embodiments, the first glass braze 141 has a glass transition temperature that is at least 50 degrees centigrade different than the second glass braze 142 glass transition temperature.

Figure 7:
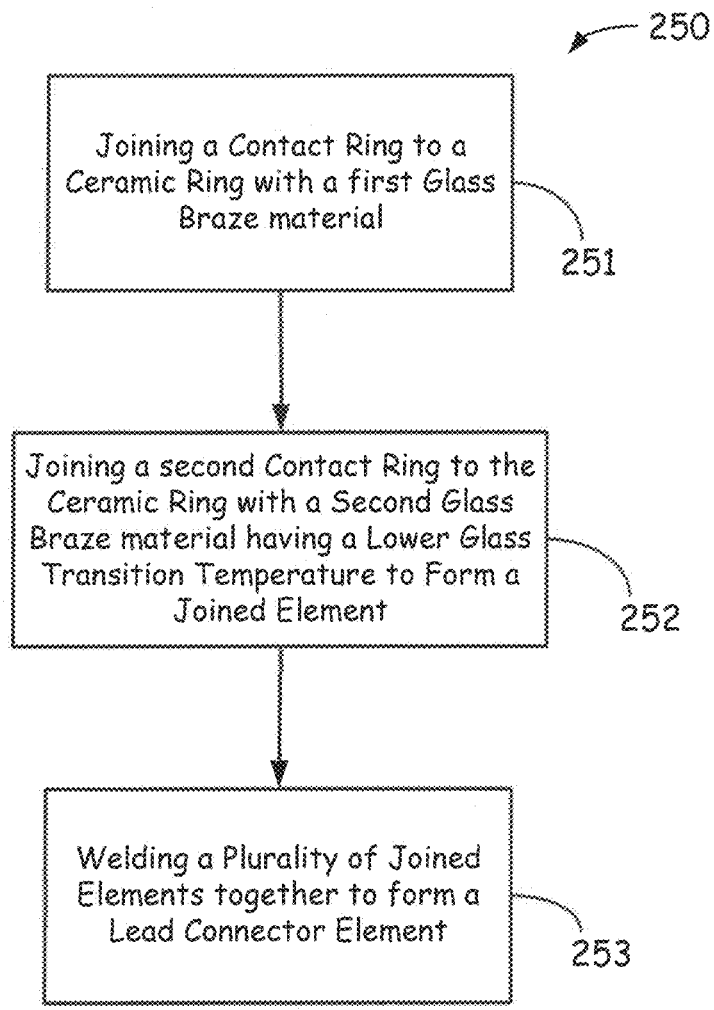
FIG. 7 is a flow diagram of an illustrative method of making a lead connector element.

FIG. 7 is a flow diagram of an illustrative method 250 of making a lead connector element. The method includes joining an electrically conducting contact ring to a ceramic insulating ring with a first glass braze material having a first glass transition temperature to form a first joined element at block 251. The method includes joining an electrically conducting spacer ring to the ceramic insulating ring of the first joined element with a second glass braze material having a second glass transition temperature to form a second joined element at block 252. The second glass transition temperature is less than the first glass transition temperature. A plurality of joined elements are then welded together to form the lead connector element at block 253.

Utilizing this method provides advantages with forming the lead connector element. One advantage of certain embodiments is that once the first glass braze joint is formed, the part can be rotated to form the second glass braze joint. Since the second glass braze joint is applied at a temperature less then the glass transition of the first glass braze joint, the first glass braze joint does not re-flow and is stable as the second glass braze joint is formed.

Thus, embodiments of the LEAD CONNECTOR WITH GLASS BRAZE are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical device lead connector comprising:
    a ring subassembly comprising:
    an electrically conducting contact ring and an electrically conducting spacer ring spaced apart by an electrically insulating ceramic ring;
    a first electrically insulating glass material directly fixing electrically conducting contact ring and the electrically insulating ceramic ring and forming a hermetic bond; and
    a second electrically insulating glass material directly fixing the electrically conducting spacer ring and the electrically insulating ceramic ring and forming a hermetic bond;
    wherein the first electrically insulating glass material is different than the second electrically insulating glass material.

2. A medical device lead connector according to claim 1, wherein the lead connector comprises a plurality of ring subassemblies fixed in axial alignment.

3. A medical device lead connector according to claim 2, wherein adjacent ring subassemblies are welded together for form a rigid medical device lead connector.

4. A medical device lead connector according to claim 1, wherein the glass insulating material comprises:
    30 mol % $B_2O_3$;
    30 to 40 mol% CaO, MgO, SrO, or combinations thereof;
    5 mol % $La_2O_3$;
    10 mol % SiO2; and
    15 mol % $Al_2O_3$.

5. A medical device lead connector according to claim 1, wherein the first electrically insulating glass material has a glass transition temperature that is at least 50 degrees centigrade different than the second electrically insulating glass material glass transition temperature.

6. An implantable active medical device comprising;
    a hermetically sealed housing defining a sealed housing interior;
    a power source and electronics in electrical communication and disposed within the sealed housing interior; and
    a lead connector projecting into the sealed housing interior and having a closed end, an open end, an outer surface, and an inner surface defining a lead aperture, the lead connector comprising a ring subassembly comprising an electrically conducting contact ring and an electrically conducting spacer ring spaced apart by an electrically insulating ring, the electrically conducting contact ring and the electrically insulating ceramic ring hermetically joined together with a first electrically insulating glass material, and the electrically conducting spacer ring and the electrically insulating ceramic ring hermetically joined together with a second electrically insulating glass material, wherein the first electrically insulating glass material has a different glass transition temperature than the second electrically insulating glass material;
    the electrically conducting contact ring and an electrically conducting spacer ring in electrical communication with the electronics, and the first and the second electrically insulating glass material providing a hermetic seal between the lead connector outer surface and the lead connector inner surface.

7. An implantable active medical device according to claim 6, wherein the lead connector comprises a plurality of ring subassemblies fixed in axial alignment.

8. An implantable active medical device according to claim 7, wherein each ring subassembly comprises the electrically insulating glass material fixing an electrically insulating ring between an electrically conducting contact ring and an electrically conducting spacer ring.

9. An implantable active medical device according to claim 8, wherein the electrically insulating glass material directly bonds the electrically conducting contact ring and the electrically conducting spacer ring with the electrically insulating ring.

10. An implantable active medical device according to claim 6, wherein the glass insulating material comprises:
    30 mol % $B_2O_3$;
    30 to 40 mol% CaO, MgO, SrO, or combinations thereof;
    5 mol % $La_2O_3$;
    10 mol % $SiO_2$; and
    15 mol % $Al_2O_3$.

11. An implantable active medical device according to claim 6, wherein the glass insulating material has a glass transition temperature of less than 700 degrees centigrade.

12. An implantable active medical device according to claim 6, wherein the first electrically insulating glass material has a glass transition temperature that is at least 50 degrees centigrade different than the second electrically insulating glass material has a glass transition temperature.

13. A method of forming a medical device lead connector comprising:
    joining an electrically conducting contact ring to a ceramic insulating ring with a first electrically insulating glass material having a first glass transition temperature to form a first joined element;
    joining an electrically conducting spacer ring to the ceramic insulating ring of the first joined element with a second electrically insulating glass material having a second glass transition temperature to form a second joined element, the second glass transition temperature being less than the first glass transition temperature.

14. A method of forming a medical device lead connector according to claim 13, further comprising welding a plurality of joined elements in axial alignment to form a lead connector element.

15. A method of forming a medical device lead connector according to claim 13, wherein the second glass transition temperature is at least 50 degree centigrade less than the first glass transition temperature.

16. A method of forming a medical device lead connector according to claim 14, further comprising placing the lead connector element within a hermetic envelope of an active medical device.

17. A method of forming a medical device lead connector according to claim 14, further comprising electrically connecting the lead connector element to a feedthrough of an active medical device.

\* \* \* \* \*